United States Patent [19]

Bru et al.

[11] Patent Number: 5,219,846
[45] Date of Patent: Jun. 15, 1993

[54] TREATMENT OF HUMAN TUMORS UTILIZING COMPOUNDS HAVING A PHOSPHOAMIDES LINKAGE OR ENOL PHOSPHATE LINKAGE

[76] Inventors: Nicole Bru, 24, Avenue Raphael, 75016 Paris; Victor Izrael, 16, rue Ernest Cresson, 75014 Paris, both of France

[21] Appl. No.: 811,058

[22] Filed: Dec. 20, 1991

[30] Foreign Application Priority Data

Dec. 3, 1991 [FR] France ................. 91 14967

[51] Int. Cl.$^5$ ............................. A61K 31/66
[52] U.S. Cl. ...................... 514/118; 514/120
[58] Field of Search ................. 514/118, 120

[56] References Cited

PUBLICATIONS

Chemical Abstracts 103:116013f (1985).

Primary Examiner—Jerome D. Goldberg
Attorney, Agent, or Firm—Dennison, Meserole, Pollack & Scheiner

[57] ABSTRACT

A method for treatment of human tumors which are sensitive to the compounds recited below, particularly those which have become resistant to chemotherapy. The method comprises administering an effective amount of creatine phosphate or phosphoenolpyruvic acid.

7 Claims, No Drawings

TREATMENT OF HUMAN TUMORS UTILIZING COMPOUNDS HAVING A PHOSPHOAMIDES LINKAGE OR ENOL PHOSPHATE LINKAGE

The present invention relates to compounds having a phosphoamide linkage or an enol phosphate linkage for their first application as therapeutically active substances.

In the framework of the present description, compound having a phosphoamide linkage is understood as meaning any compound whose chemical structure contains a group

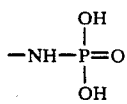

A preferred example of such compounds is creatine phosphate, also called phosphocreatine, which is a widespread substance in vertebrates and is present especially in the striated muscle but absent from the blood and extracellular fluids. Another example is arginine phosphate, which is found in the muscles of invertebrates.

Likewise, compound having an enol phosphate linkage is understood as meaning any compound whose chemical structure contains the group

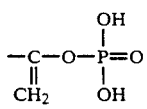

A preferred example of such compounds is phosphoenolpyruvic acid, which is an intermediate endogenous metabolite involved in glycolysis and which, under physiological conditions, is therefore localized in the cells and absent from the blood.

The phosphoamide or enol phosphate linkages of the afore-mentioned compounds are energy-rich linkages.

It has been discovered that compounds having a phosphoamide linkage or an enol phosphate linkage possess particularly valuable pharmacological properties and especially a particularly remarkable antitumoral activity; it is this discovery which forms the basis of the present invention.

These compounds will therefore have applications especially in the treatment of human tumors sensitive thereto and more particularly in the treatment of tumors immediately after onset or those which have become resistant to chemotherapy, such as, for example: adenocarcinomas (colon, pancreas, stomach, bronchi, kidneys, breasts, uterus, ovaries); epidermoid carcinomas (upper respiratory-digestive tract, bronchi, urinary tract, anus, skin); malignant melanoma; soft tissue sarcomas; leukemias; lymphomas; and multiple myeloma.

Thus the present invention covers the pharmaceutical compositions, especially those with antitumoral activity, in which at least one compound having a phosphoamide linkage or an enol phosphate linkage is present as the active ingredient in association with a pharmaceutically acceptable excipient.

These pharmaceutical compositions will generally be prepared by conventional methods and administered venously, in the form of a bolus or an intermittent or continuous perfusion, intraarterially, intraperitoneally or intramuscularly, at doses which can vary from 50 mg to 5 g per kilogram of body weight per 24 hours.

The invention also aims to cover a method of preparing a pharmaceutical composition, especially one with antitumoral activity against human tumors sensitive thereto, which consists in incorporating a pharmaceutically effective amount of at least one compound having a phosphoamide linkage or an enol phosphate linkage into a pharmaceutically acceptable excipient.

According to a particular characteristic of this method, the pharmaceutical composition is formulated as an injectable preparation containing from 0.1 to 50 g of active ingredient.

Finally, the present invention also aims to cover a method of treating human tumors sensitive to the recited compounds, which comprises administering a therapeutically effective amount of at least one compound having a phosphoamide linkage or an enol phosphate linkage.

The pharmacological properties of the compounds having a phosphoamide linkage or an enol phosphate linkage were demonstrated by using different studies to evaluate the effects of creatine phosphate on tumoral cells.

The effects observed are indisputably due to the presence of a phosphoamide linkage in this molecule.

Complementary tests on phosphoenolpyruvic acid suggest that analogous pharmacological properties can be obtained from compounds having an enol phosphate linkage.

1. METHOD

1.1 Principle

The development of an adenocarcinoma of human origin in nude mice is effected by the inoculation of $CaCO_2$ cancerous cells. The effects of creatine phosphate on the tumoral growth and the cell differentiation are studied after intravenous or intraperitoneal administration of the product. These effects are evaluated by measurement of the size and weight of the tumor and then by histological examination, the data for the control group being compared with those for the treated group.

1.2 PROCEDURE

1.2.1 Preparation of the Animal

4-Week-old nude mice of the Swiss strain are kept in isolation for one week before implantation of the tumoral cells under sterile conditions.

1.2.2 Cell Culture

The $CaCO_2$ cells are cultivated in DMEM containing 20% of fetal calf serum, 2 mM glutamine and 1% of non-essential amino acids, in an incubator with 10% of $CO_2$. The culture medium is renewed 3 times a week. Subculture is carried out using trypsin and EDTA.

1.2.3 Development of the Adenocarcinoma of Human Origin in Nude Mice

After treatment with trypsin, each host mouse is inoculated subcutaneously in the right side with an amount of about $10 \times 10^6$ $CaCO_2$ cells (either in 0.2 ml of PBS or in 0.2 ml of culture medium) under sterile conditions. The animals are then kept in isolation.

The animals are weighed and the tumor is measured with a sliding caliper every day in order to establish a curve of tumoral growth. The volume of the tumor established in this way (hemiellipsoidal) is calculated according to the following formula:

$$\text{volume} = 0.5236 \times \text{width} \times \text{length} \times \text{height}$$
(Dethlefsen et al., 1968)

When the animal is sacrificed, the entire tumor is removed, weighed and then fixed in 10% formalin or Bouin's fixative for anatomicopathological examination.

1.2.4 Study of the Effect of Creatine Phosphate on the Growth and Tumoral Differentiation Two series of studies were carried out with creatine phosphate.

Each series comprises 7 or 8 nude mice divided up into control and treated groups. At the start of the study, all the mice received a subcutaneous implant of $CaCO_2$ tumoral cells in the right side.

The treatment was commenced 7 days after implantation in the case of experiment 1 and continued for 6 weeks. The group of control animals received the vehicle under the same conditions.

In the case of experiment 2, the animals were treated during the exponential phase of tumoral growth, namely 6 weeks after injection of the tumoral cells and for 3 and a half weeks.

The dosage was as follows:

0.5M creatine phosphate dissolved in 0.9% NaCl, injected in a volume of 1 ml at a rate of 6 intraperitoneal injections per week (treated group), 1 ml of isotonic solution (0.9% NaCl) per injection at a rate of 6 injections per week (control group).

For the first series, the animals were sacrificed one week after cessation of the treatment and the tumors removed were fixed in 10% formalin. For the second series, the animals were sacrificed at cessation of the treatment and the tumors removed were fixed in Bouin's fixative.

2. RESULTS

The results are shown in the Table below and indicate the weight of the tumor in mg for each individual animal.

neoplasms removed from the control animals, the size of the tumors observed in the treated animals is very appreciably smaller. No notable difference is visible as regards the observed architecture and cytology of the neoplasms.

3. CONCLUSION

Depending on the series in question, the results show an inhibition of the tumoral growth or a tumoral regression after the administration of creatine phosphate to nude mice with established tumors.

TOLERANCE

Creatine phosphate was administered intravenously to rats once a day for 5 days at doses of 600, 1200, 1800 and 2400 mg/kg. The weight change and the eating behavior of the animals were followed over the experimental period. A biochemical and hematological evaluation was performed on the plasma and blood collected after the animals had been sacrificed.

Under the experimental conditions described, creatine phosphate did not induce mortality.

The variations observed relate to the groups of animals treated with the highest doses studied, which cause a modest increase in the transaminases and the sodium and a decrease in the alkaline phosphatases and the formed elements of the blood.

The other modifications are in keeping with the fluctuations normally encountered in rats.

Creatine phosphate displayed an excellent biological tolerance at doses which can range up to 2400 mg, administered intravenously.

Likewise, phosphoenolpyruvic acid displayed a good biological tolerance and was administered to rats in doses of up to 500 mg/kg without inducing mortality.

Non-limiting Examples of pharmaceutical compositions based on a compound having a phosphoamide linkage or an enol phosphate linkage will be found below.

Creatine phosphate can be either in the form of a ready-to-use sterile solution or in the form of a sterile powder or lyophilizate. In this case, it may be advantageous to use a bulking agent with no pharmacological

|  | CONTROL ANIMALS | | | ANIMALS TREATED WITH UP 999-247 | | |
| --- | --- | --- | --- | --- | --- | --- |
|  | Body weight (g) | | | Body weight (g) | | |
|  | Start of test | End of test | Weight of the tumor (mg) | Start of test | End of test | Weight of the tumor (mg) |
| Experiment 1 | 17 | 22 | 577.2 | 18.5 | 23.5 | 88.9 |
|  | 16.5 | 23 | 812.6 | 20 | 24 | 33.4 |
|  | 16.5 | 21.5 | 20.5 | 18 | 21 | 84.2 |
|  | 16 | 22 | 47.2 |  |  |  |
| Experiment 2 (*) | 27.5 | 33 | 2274 | 24.5 | 26 | 287 |
|  | 25 | 31.5 | 2240 | 24.5 | 29 | 818 |
|  | 23 | 27 | 103 | 26 | 28.5 | 184 |
|  |  |  |  | 23 | 28 | 97 |
|  |  |  |  | 21.5 | 24 | 10 |

(*) The average weight increase during the treatment is 3.2 g for the treated animals and 5.0 g for the control animals.

The results obtained show that there is no difference between the control group and the treated group from the point of view of behavior and general state. An important difference is observed between the two groups, in the two series tested, as regards the weight of the tumor removed.

As far as the histological examination is concerned, the specimens removed are identified as adenocarcinomas with little differentiation. Compared with the activity, especially lactose or mannitol.

The reconstitution solvent may either be selected from the injection solvents in conventional use (9%. NaCl, serum containing 5% or 15% of glucose, sorbitol) or be any other generally available perfusion solvent.

Preferably, the pharmaceutical preparation will take the form of a sterile lyophilizate containing 25 g of creatine phosphate to be reconstituted with 100 ml of a 9‰. solution of sodium chloride.

What is claimed is:

1. A method for the treatment of human tumors sensitive to treatment with the compounds below, comprising administering to a human in need thereof an effective amount of a compound selected from the group consisting of creatine phosphate and phosphoenolpyruvic acid, said administering taking place venously, in the form of a bolus or an intermittent or continuous perfusion, intraarterially, intraperitoneally or intramuscularly.

2. The method of claim 1, wherein the tumor is an adenocarcinoma, epidermoid carcinoma, malignant melanoma, soft tissue sarcoma, leukemia, lymphoma or multiple myeloma.

3. The method of claim 1, wherein said effective amount is between 50 mg and 5 g per kilogram of body weight per 24 hours.

4. The method of claim 1, wherein said administering takes place by injection.

5. The method of claim 1, wherein said compound is creatine phosphate.

6. The method of claim 1, wherein said compound is phosphoenolpyruvic acid.

7. A method for treatment of adenocarcinoma or malignant melanoma in humans, comprising administering to a human in need thereof an effective amount of a compound selected from the group consisting of creatine phosphate and phosphoenolpyruvic acid, said administering taking place venously, in the form of a bolus or an intermittent or continuous perfusion, intraarterially, intraperitoneally or intramuscularly.

* * * * *